United States Patent [19]

Matsutani et al.

[11] Patent Number: 5,155,943
[45] Date of Patent: Oct. 20, 1992

[54] SUTURE NEEDLE AND METHOD OF AN APPARATUS FOR GRINDING MATERIAL FOR SUTURE NEEDLE

[75] Inventors: Kanji Matsutani; Tadashi Otsuka; Yoshimasa Tochimura, all of Takanezawa, Japan

[73] Assignee: Matsutani Seisakusho Co., Ltd., Tochigi, Japan

[21] Appl. No.: 822,919

[22] Filed: Jan. 21, 1992

Related U.S. Application Data

[63] Continuation of Ser. No. 638,220, Jan. 9, 1991, abandoned.

[30] Foreign Application Priority Data

Jan. 12, 1990 [JP] Japan ................................ 2-3471

[51] Int. Cl.$^5$ .............................................. B24B 1/00
[52] U.S. Cl. ..................... 51/281 R; 51/326; 51/328; 51/227 H; 51/62; 51/63; 163/5
[58] Field of Search ............ 51/57, 59 R, 62, 63, 51/70, 135 R, 142, 227 H, 281 R, 289 R, 326, 328, 357, 359, 360, 361; 163/5

[56] References Cited

U.S. PATENT DOCUMENTS

| | | |
|---|---|---|
| 1,599,059 | 9/1926 | Morton . |
| 2,802,310 | 8/1957 | Chaplik ........................ 51/227 H |
| 3,427,764 | 2/1969 | Draving ........................ 51/324 |
| 3,545,138 | 12/1970 | Houston ........................ 51/59 |
| 4,048,761 | 9/1977 | Cottrell ........................ 51/142 |
| 4,320,892 | 3/1982 | Longbrake ...................... 269/3 |
| 4,651,471 | 3/1987 | Makino et al. .................. 51/326 |
| 4,850,147 | 7/1989 | Baker ........................... 51/326 |

FOREIGN PATENT DOCUMENTS

| | | |
|---|---|---|
| 51-39420 | 9/1976 | Japan . |
| 55-41208 | 9/1980 | Japan . |
| 60-135106 | 9/1985 | Japan . |
| 61-6885 | 3/1986 | Japan . |
| 63-35383 | 7/1988 | Japan . |
| 906205 | 9/1962 | United Kingdom . |

Primary Examiner—M. Rachuba
Attorney, Agent, or Firm—Wegner, Cantor, Mueller & Player

[57] ABSTRACT

There are disclosed a method of and apparatus for grinding an elongated material for a suture needle. An elongated grinding tape is reciprocally moved in its longitudinal direction, and simultaneously the material is pressed against the grinding tape in such a manner that the material is disposed substantially perpendicular to the longitudinal direction of the grinding tape and is inclined relative to one face of the grinding tape, thereby grinding the material to form a cutting edge on at least one side edge of a grounded surface of the material. The grinding apparatus includes a mechanism for reciprocally moving the grinding tape in opposite directions along the longitudinal direction of the grinding tape, a mechanism for transferring the grinding tape in a predetermined one of the opposite directions along the longitudinal direction of the grinding tape, a tape support member, and a mechanism for supporting the material and for pressing the material against that portion of the grinding tape positioned at a support surface of the tape support member. A suture needle includes at least one ground surface, and a pair of cutting edges formed respectively on opposite side edges of the ground surface. The ground surface has grinding traces which extend perpendicular to an axis of the suture needle, and the pair of cutting edges are in generally the same condition from a microscopic point of view.

4 Claims, 4 Drawing Sheets

SUTURE NEEDLE AND METHOD OF AN APPARATUS FOR GRINDING MATERIAL FOR SUTURE NEEDLE

This application is a continuation of U.S. application Ser. No. 07/638,220, filed Jan. 9, 1991, now abandoned.

BACKGROUND OF THE INVENTION

This invention relates to a suture (surgical) needle and a method of and apparatus for grinding a needle material to form a suture needle having a cutting edge.

A general method of producing a suture needle having a cutting edge will now be briefly described.

First, a wire is cut into a predetermined length to provide an elongated needle material. Then, a mounting hole to which a gut is to be attached is formed in one end portion of the needle material. Then, the needle material is pressed into a required cross-sectional shape. Then, the needle material is ground to form a cutting edge. Then, the needle material is bent into a required shape. Then, the needle material is subjected to a heat treatment, and then is subjected to chemical polishing and/or electropolishing. Finally, a silicone coating is optionally applied to the needle thus produced.

Japanese Patent Publication No. 35383/88 discloses one method of grinding a needle material. This method will now be described in detail with reference to FIG. 14. In this method, there are used a whetstone 90 with a cylindrical peripheral surface and a chucking jig 91. A needle material 100 having a mounting hole formed in its one end portion is chucked or held by the chucking jig 91, and is pressed against the peripheral surface of the whetstone 90 in such a manner that the needle material 100 is oriented perpendicular to an axis 90a of rotation of the whetstone 90. The needle material 100 is ground by the rotation of the whetstone 90, and as a result a cutting edge is formed at one or each of lateral edges of the ground surface of the needle material, and at the same time the end of the needle material remote from the one end portion thereof chucked by the chucking jig 91 is pointed.

This method has the following disadvantages (1) to (4):

(1) The grinding direction (that is, the direction of movement of abrasive grains bonded to the peripheral surface of the whetstone) is generally parallel to the longitudinal direction of the needle material, and hence is substantially parallel to the cutting edge produced by the grinding. Therefore, burrs formed on the cutting edge are considerably large. When these burrs are to be removed by electropolishing or chemical polishing, it is difficult to determine a proper time for such polishing treatment. More specifically, if the treatment time is too short, the burrs fails to be removed to a satisfactory level, and in contrast if the treatment time is too long, the cutting edge becomes rounded. In either case, the piercing properties of the resultant suture needle are adversely affected.

Figure 14:
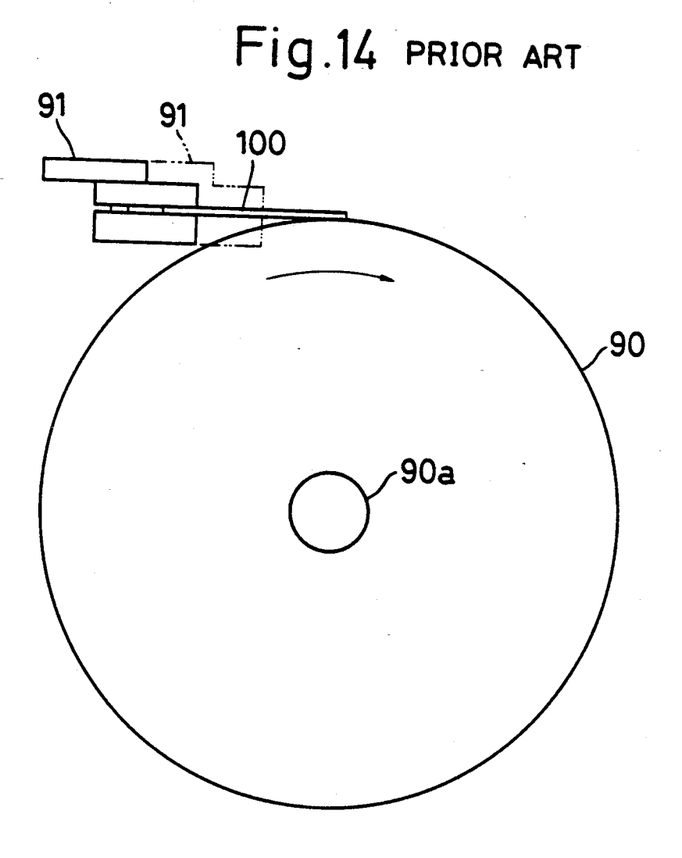
FIG. 14 is a front-elevational view of a conventional grinding apparatus.

(2) The direction of rotation of the whetstone 90 during the grinding is so determined that the abrasive grains bonded to the peripheral surface of the whetstone 90 move in a direction away from the chucked end of the needle material 100 toward the pointed end thereof. The reason for this is to prevent the pointed end of the needle material 100 from interfering with the peripheral surface of the whetstone 90. However, with this rotation direction, the heat produced by the grinding concentrates on the pointed end of the needle material 100, having a small heat capacity, to soften the pointed end of the needle material 100, so that the piercing properties and strength of the resultant suture needle are adversely affected.

(3) The condition of the peripheral surface of the whetstone 90 is changed little by little in the course of a long-period use, and as a result the condition of the cutting edge obtained by the grinding is changed little by little from one needle material to another.

(4) As shown in FIG. 14, when the needle material 100 is pressed against the peripheral surface of the whetstone 90, the chucking jig 91 must be held apart from the peripheral surface of the whetstone 90. This does not pose any problem when grinding the needle material for a long suture needle, but poses a problem when grinding the needle material for a short suture needle used for an operation on the eye. When the needle material is short, the chucking jig 91 must be located at a position shown in phantom in FIG. 14; however, at this position, the chucking jig 91 interferes with the whetstone 90. Therefore, actually, the chucking jig 91 is located at the position shown in a solid line in FIG. 14, and the needle material must be much longer than the resultant suture needle. This requires an additional step of cutting the needle material after the grinding step, and after this cutting step, the step of forming the mounting hole in the end of the needle material must be carried out. During the cutting step and the mounting hole-forming step, it is possible that the cutting edges of a number of the needle materials are contacted with one another, and are damaged, which adversely affects the piercing properties of the cutting edges. And besides, because of the additional cutting step and the waste of the material, the manufacturing cost of the suture needle is increased.

In another conventional method of grinding a needle material, there is used an endless abrasive sheet extended around a pair of rollers. This abrasive sheet comprises a sheet-like substrate made of a cloth, paper or the like, and abrasive grains bonded to an outer surface of this substrate. In this method, a chucking jig disposed near the peripheral surface of the roller chucks the needle material in such a manner that the needle material is oriented in parallel relation to the direction of movement of the abrasive sheet, and the needle material is pressed against that portion of the abrasive sheet extended around the peripheral surface of the roller. This method also has the above-mentioned disadvantages (1) to (4).

Japanese Utility Model Publication Nos. 39420/76, 41208/80 and 6885/86 and Japanese Laid-Open (Kokai) Utility Model Application No. 135106/85 disclose suture needles having a number of grinding traces extending perpendicular to a cutting edge. Although a grinding method is not clearly described in these prior art publications, it is clear that abrasive grains move in a direction perpendicular to the cutting edge to effect the grinding. In such method, the above disadvantage (2) is overcome, and probably the above disadvantage (4) may be overcome. However, the above disadvantage (3) is not overcome, and instead of the above disadvantage (1), another disadvantage is encountered. More specifically, large burrs are formed on one of the two cutting edges which is disposed at a downstream side of the direction of movement of the abrasive grains, the two cutting edges being formed respectively on the lateral edges of the ground surface of the needle material. Burrs are hardly formed on the other cutting edge disposed at an upstream side of the direction of movement of the abrasive grains. Therefore, when the burrs on the downstream-side cutting edge are removed by electropolishing or chemical polishing after the grinding operation, the upstream-side cutting edge becomes rounded. This adversely affects the piercing properties of the resultant suture needle.

SUMMARY OF THE INVENTION

It is an object of this invention to provide a suture needle and a method of and apparatus for grinding a needle material for a suture needle, which overcome the above deficiencies of the prior art.

According to one aspect of the present invention, there is provided a method of grinding an elongated material for a suture needle, comprising the step of reciprocally moving an elongated grinding tape in opposite directions along a longitudinal direction of the grinding tape, and simultaneously pressing the material against one face of the grinding tape in such a manner that the material is disposed substantially perpendicular to the longitudinal direction of the grinding tape and is inclined relative to the one face of the grinding tape, thereby grinding the material to form a cutting edge on at least one side edge of a grounded surface of the material.

According to another aspect of the present invention, there is provided a grinding apparatus for grinding an elongated material for a suture needle, comprising:
(a) an elongated grinding tape;
(b) reciprocal movement means for reciprocally moving the grinding tape in opposite directions along a longitudinal direction of the grinding tape;
(c) transfer means for transferring the grinding tape in a predetermined one of the opposite directions along the longitudinal direction of the grinding tape;
(d) a tape support member having a support surface along which the grinding tape is moved; and
(e) pressing means for supporting the material in such a manner that the material is disposed substantially perpendicular to the longitudinal direction of the grinding tape and is inclined relative to one face of the grinding tape, and for pressing the material against that portion of the grinding tape positioned at the support surface of the tape support member.

According to a further aspect of the present invention, there is provided a suture needle including at least one ground surface, and a pair of cutting edges formed respectively on opposite side edges of the ground surface, the ground surface having grinding traces which extend perpendicular to an axis of the suture needle, and the pair of cutting edges being in generally the same condition from a microscopic point of view.

DESCRIPTION OF THE PREFERRED EMBODIMENTS OF THE INVENTION

Figure 8:
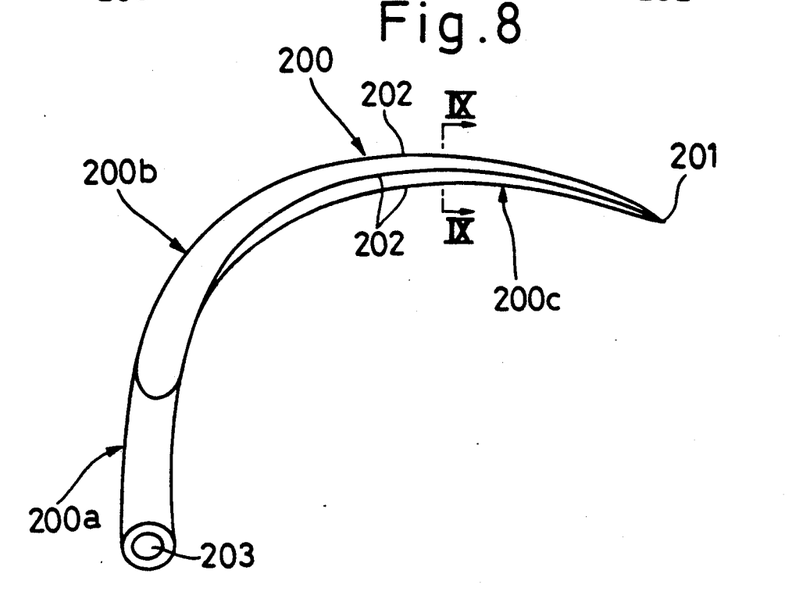
FIG. 8 is a perspective view of a suture needle obtained by bending the ground needle material.
Figure 9:
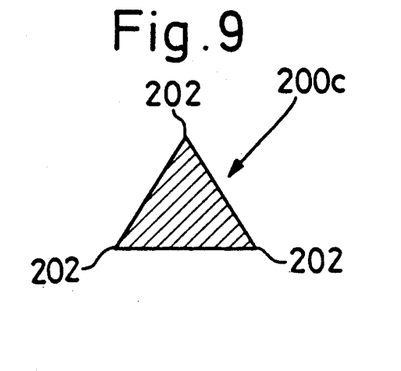
FIG. 9 is a cross-sectional view taken along the line IX—IX of FIG. 8.
Figure 10:
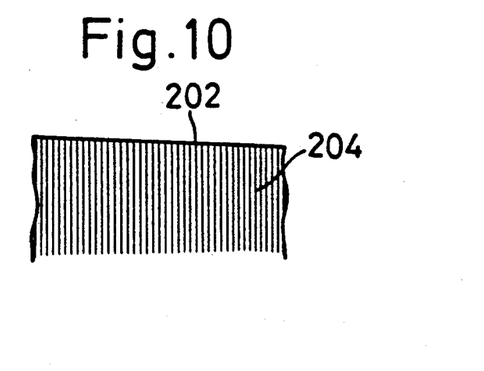
FIG. 10 is a fragmentary, enlarged view of the needle material, showing a cutting edge and grinding traces formed on the needle material.

Before describing a method and apparatus of the present invention, a suture needle (final product) 200 will be first described in detail with reference to FIGS. 8 to 10. The suture needle 200 includes a first portion (proximal end portion) 200a of a circular cross-section, an intermediate portion 200b of a triangular cross-section generally uniform in cross-sectional area throughout an entire length of the intermediate portion 200b, and a third portion (distal end portion) 200c of a triangular cross-section decreasing in cross-sectional area progressively toward a pointed end 201. The third portion 200c has three ground surfaces, and each of the three edges of the third portion 200c defined by intersection between respective two adjacent ground surfaces serves as a sharp cutting edge 202. The three cutting edges 202 are generally in the same condition from a microscopic point of view. Namely, when burrs remain on the three cutting edges in an allowable range, the burrs on these cutting edges are of generally the same size. And, when the burrs hardly remain on the three cutting eges 202, these cutting edges are rounded to generally the same level. Grinding traces 204 are formed on each of the three ground surfaces, and extend in a direction perpendicular to the axis of the suture needle, and intersect the cutting edge 202. A blind hole is formed in the proximal end face of the suture needle 200, and extends along the axis of the proximal end portion 200a. This blind hole serves as a mounting hole 203 to which a gut is to be attached. The mounting hole may be constituted by a through hole extending transversely through the proximal end portion 200a perpendicularly to the axis thereof.

The dimensions of the suture needle 200 are not particularly limited. For example, the suture needle 200 has a thickness of 0.07 to 1.4 mm and a length of 4 to 65 mm, and particularly the suture needle 200 has a thickness of 0.07 to 0.33 mm and a length of 4 to 13 mm for use in an operation on the eye.

Next, the method of producing the suture needle 200 will now be described briefly. A wire of austenite-type stainless steel is cold-drawn into a required diameter, with its crystals converted into a fiber-like structure. Then, this wire is cut into a predetermined length to provide an elongated stock of a circular cross-section. The stock may be composed of martensite-type stainless steel or precipitation hardened stainless steel.

Figure 6:
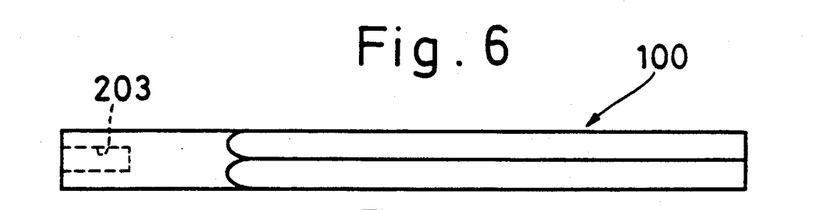
FIG. 6 is a side-elevational view of a needle material with its diameter shown as exaggerated.

The length of the stock is generally equal to the length of the suture needle (final product) 200. More exactly, the stock is slightly longer than the suture needle 200, taking into consideration that amount of the stock to be lost by the grinding. A laser beam or an electron beam is applied to the proximal end face of the stock to form the mounting hole 203 (FIG. 6). Then, the stock is shaped by pressing into a triangular cross-section except for that portion thereof (proximal end portion) where the mounting hole 203 is formed, thereby providing a needle material 100 shown in FIG. 6. The pressed portion of the needle material 100 has a generally uniform triangular cross-sectional area throughout an entire length thereof. For obtaining the needle material 100, the stock may be shaped into a triangular cross-section by grinding, instead of the pressing. Then, the three side faces of the cross-sectionally triangular portion are ground according to the procedure of the present invention, thereby forming the three cutting edges 202 and the pointed end 201. Then, the needle material 100 thus ground is bent to thereby obtain the suture needle 200 as shown in FIG. 8. Thereafter, the suture needle 200 is subjected to a heat treatment, and then to chemical polishing and/or electropolishing.

Figure 1:
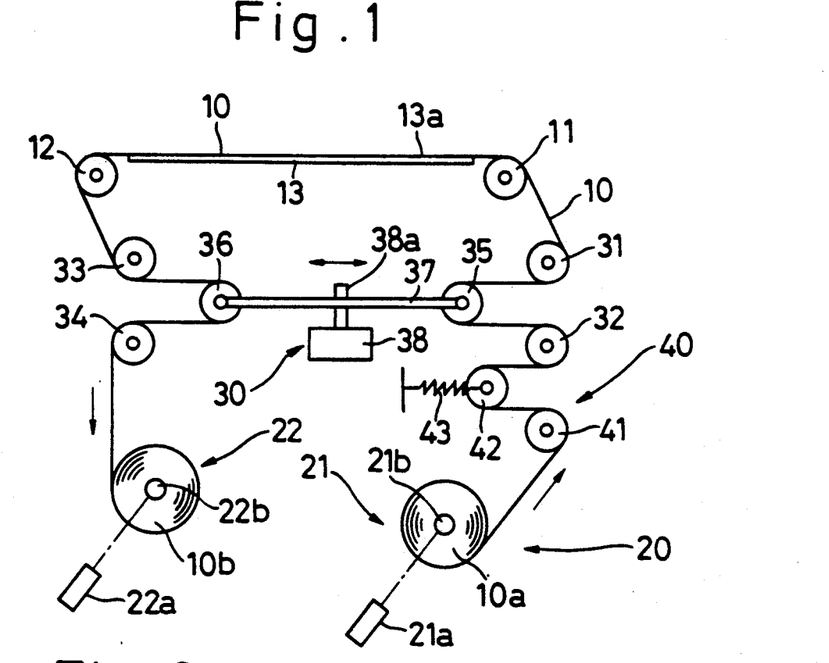
FIG. 1 is a schematic front-elevational view of a grinding apparatus according to the present invention.
Figure 2:
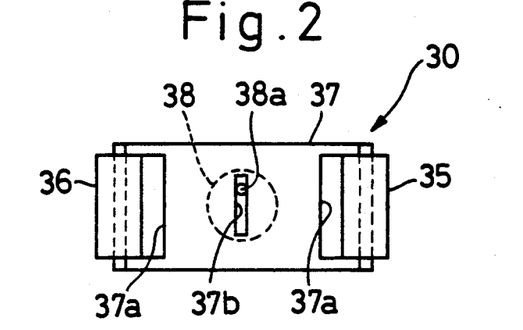
FIG. 2 is a plan view of a reciprocal movement mechanism of the grinding apparatus.
Figure 3:
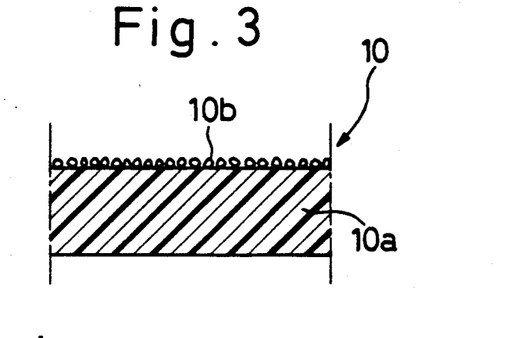
FIG. 3 is an enlarged transverse cross-sectional view of a grinding tape.

Next, a grinding apparatus for grinding the needle material 100 in the above-mentioned manner will now be described with reference to FIGS. 1 to 5. As shown in FIG. 1, this grinding apparatus includes a long grinding tape 10. As shown in FIG. 3, the grinding tape 10 comprises a tape body or substrate 10a made of a synthetic resin such as polyester. The tape body 10a has a thickness of 0.1 mm, a width of 12.5 to 25 mm, and a length of 50 to 100 m, and has a smooth surface. Abrasive grains 10b, such as white alundum (WA), having a grain size of 1300 to 2000 (4 to 14 micron meter diameter) are bonded to the smooth surface of the tape body 10a by a binder resin (not shown). The size of the abrasive grains 10b of the grinding tape 10 is determined, taking into consideration the grinding of the needle material 100 for the suture needle 200 of a very small size. The tape body 10a may be made of metal.

The grinding apparatus comprises a pair of guide rollers 11 and 12 for guiding the grinding tape 10, these guide rollers being spaced from each other in a horizontal direction. The guide rollers 11 and 12 are disposed at the same height or level, and a back-up plate 13 serving as a tape support member is horizontally provided between the guide rollers 11 and 12. A flat upper surface of the back-up plate 13 is disposed at the same height as those of the top points of the guide rollers 11 and 12, and serves as a support surface 13a. Part of the grinding tape 10 is placed on the back-up plate 13 in such a manner that the surface of that part having the abrasive grains 10a bonded thereto is directed upwardly.

The grinding apparatus is provided with a transfer mechanism 20 for transferring or moving that portion of the grinding tape 10, which is placed on the back-up plate 13, in a predetermined direction (that is, in a left-hand direction in FIG. 1) which is the longitudinal direction of the grinding tape 10. The transfer mechanism 20 comprises a feed mechanism 21 for feeding a fresh or unused grinding tape 10 to the back-up plate 13, and a take-up mechanism 22 for taking up or winding up the used grinding tape 10 fed from the back-up plate 13. More specifically, the feed mechanism 21 is disposed below the guide roller 11, and comprises a motor 21a with a brake, and a rotation shaft 21b connected to the motor 21a. The take-up mechanism 22 is disposed below the other guide roller 12, and comprises a motor 22a with a brake, and a rotation shaft 22b connected to the motor 22a. A roll 10a of the unused grinding tape 10 is supported on the rotation shaft 21b of the feed mechanism 21. A roller 10b of the used grinding tape 10 is supported on the rotation shaft 22b of the tape-up mechanism 22. The grinding tape 10 is fed or supplied from the roll 10a is passed past the guide roller 11, the back-up plate 13 and the guide roller 12, and reaches the roll 10b.

The grinding apparatus is provided with a reciprocal movement mechanism 30 for reciprocally moving that portion of the grinding tape 10, which is placed on the back-up plate 13, in opposite directions (i.e., the right and left directions in FIG. 1) along the longitudinal direction of the grinding tape 10. The reciprocal movement mechanism 30 comprises four rollers 31, 32, 33 and 34 rotatable at their respective fixed positions, two floating rollers 35 and 36, a support plate (roller support member) 37, and a motor (drive means) 38. The rollers 31 and 32 are disposed between the guide roller 11 and the feed mechanism 21, and are vertically spaced from each other in opposed relation to each other. The rollers 33 and 34 are disposed between the guide roller 12 and the take-up mechanism 22, and are spaced from each other in opposed relation to each other. The support plate 37 is disposed between the opposed rollers 31 and 32 and the opposed rollers 33 and 34, and is supported by guide means (not shown) so as to reciprocally move in the right and left directions in FIG. 1. The support plate 37 is horizontally disposed at a level lower than the rollers 31 and 33 but higher than the rollers 32 and 34. A pair of notches 37a are formed respectively in the opposite ends of the support plate 37, and the floating rollers 35 and 36 are rotatably received in these notches 37a, respectively. That portion of the grinding tape 10 extending between the feed mechanism 21 and the guide roller 11 is extended around the roller 32, the floating roller 35 and the roller 31. That portion of the grinding tape 10 extending between the guide roller 12 and the tape-up mechanism 22 is extended around the roller 33, the floating roller 36 and the roller 34.

The motor 38 is disposed below the support plate 37. As best shown in FIG. 2, the motor 38 has an eccentric shaft 38a, and the eccentric shaft 38a is received in a slot 37b which is formed through the support plate 37 and extends in the direction of the width of the support plate 37. When the motor 38 is rotated, the support plate 37 is reciprocally moved in the right and left directions. When the support plate 37 is moved in the left direction, that portion of the grinding tape 10 extended around the right floating roller 35 is pulled whereas that portion of the grinding tape 10 extended around the left floating roller 36 is loosened, so that the grinding tape 10 on the back-up plate 13 is moved in the right direction. In contrast, when the support plate 37 is moved in the right direction, the grinding tape 10 on the back-up plate 13 is moved in the left direction. Thus, the rotation of the motor 38 causes the grinding tape 10 to reciprocally move on the back-up plate 13 in the right and left directions.

The reciprocal movement mechanism may use a cam operatively associated with the motor so as to reciprocally move the support plate, and also may use any suitable drive means, such as a pneumatic cylinder, a hydraulic cylinder and a solenoid, instead of the motor.

The grinding apparatus is provided with a tension mechanism 40. The tension mechanism 40 comprises a roller 41 rotatable at a fixed position, a floating roller 42, and a spring 43 urging the floating roller 42. The spring 43 applies a predetermined tension to the grinding tape 10 extended around the roller 41 and the floating roller 42.

Figure 4:
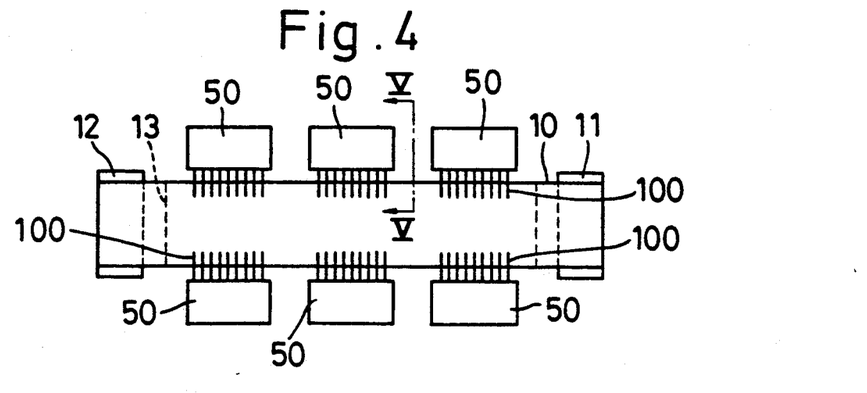
FIG. 4 is a plane view showing pressing mechanisms of the grinding apparatus arranged adjacent to the lateral sides of the grinding tape.

As shown in FIG. 4, the grinding apparatus is provided with six pressing mechanisms 50 for supporting the needle materials 100 and pressing them against the grinding tape 10. More specifically, three pressing mechanisms 50 are disposed adjacent to one lateral side of the back-up plate 13, and are juxtaposed in the longitudinal direction of the back-up plate 13. Similarly, the other three pressing mechanism 50 are disposed adjacent to the other lateral side of the back-up plate 13, and are juxtaposed in the longitudinal direction of the back-up plate 13.

Figure 5:
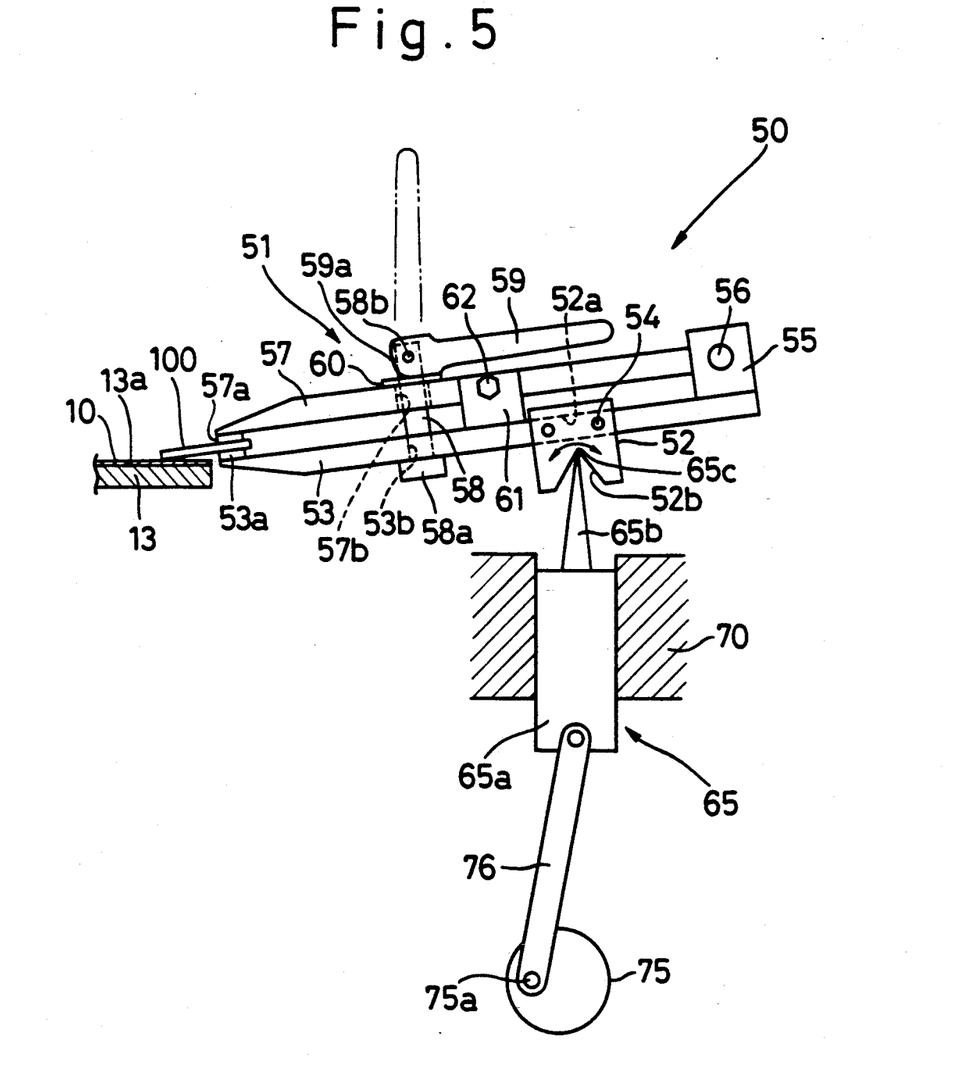
FIG. 5 is a side-elevational view of the pressing mechanism of the grinding apparatus.

As shown in FIG. 5, each of the pressing mechanisms 50 includes a chucking jig 51. The chucking jig 51 has a support rod 52 of a generally square cross-section extending in the longitudinal direction of the grinding tape 10, that is, in a direction perpendicular to the sheet of FIG. 5. The support rod 52 has a through hole 52a extending in the direction of the width thereof. A first plate 53 is passed through the through hole 52a of the support rod 52. Fixing screws 54 are threaded into one end face of the support rod 52, and are held at their distal ends against the side edge of the first plate 53, thereby fixing the first plate 53 relative to the support rod 52. A pair of guide members 55 (only one of which is shown in FIG. 5) are fixedly mounted on the upper surface of the first plate 53 at the rear end portion thereof, the guide members 55 being spaced from each other in a direction perpendicular to the sheet of FIG. 5. A sliding rod 56 is supported by the pair of guide members 55 so as to be rotated about its axis and also to slide in a direction perpendicular to the sheet of FIG. 5. A second plate 57 is fixedly secured at its rear end to the sliding rod 56. A pair of elongated elastic members 53a and 57a each made of rubber or the like and extending in a direction perpendicular to the sheet of FIG. 5 are secured respectively to the opposed surfaces of the first and second plates 53 and 57 at the distal end portions of these plates 53 and 57. A number of needle materials 100 are held between the elastic members 53a and 57a in such a manner that the needle materials 100 are disposed perpendicular to the grinding tape 10 and are juxtaposed in the longitudinal direction of the grinding tape 10. Each of the needle materials 100 is chucked or clamped by the elastic members 53a and 57a at one end portion thereof having the mounting hole 203.

Means for imparting, to the first and second plates 53 and 57, the force for clamping the needle materials 100 is as follows. A through hole 53b is formed through the intermediate portion of the first plate 53, and an elongated through hole 57b extending in a direction perpendicular to the sheet of FIG. 5 is formed through the second plate 57. A bolt 58 is passed through the two through holes 53b and 57b. A nut 58a is threaded on the lower end of the bolt 58, and a lever 59 is pivotally connected at one end thereof to the upper end of the bolt 58 through a pin 58b. The lever 59 has a cam surface 59a formed at the one end thereof, and the cam surface 59a is held in contact with a washer 60 placed on the upper surface of the second plate 57. When the lever 59 is erected, that is, moved away from the second plate 57, the force applied by the first and second plates 53 and 57 to clamp the needle materials 100 is released. When the lever 59 is laid down, that is, moved toward the second plate 57, the first and second plates 53 and 57 is supplied with the force for clamping the needle materials 100 because of the cam action achieved by the cooperation of the cam surface 59a with the washer 60.

A pair of blocks 61 (only one of which is shown in FIG. 5) are mounted on the upper surface of the first plate 53, and are spaced from each other in a direction perpendicular to the sheet of FIG. 5. A pair of set screws 62 are threaded respectively through the pair of blocks 61 from the outer sides of the blocks 61 to extend in a direction perpendicular to the sheet of FIG. 5. The distal ends of the two set screws 62 are held respectively against the lateral sides of the second plate 57, thereby positioning the second plate 57 relative to the first plate 53 in a direction perpendicular to the sheet of FIG. 5.

The pressing mechanism 50 further comprises a jig support member 65 angularly-movably supporting the chucking jig 51. The jig support member 65 includes a slider portion 65a supported by a guide member 70 so as to slide vertically (i.e., upward and downward), and a support portion 65b extending upwardly from the upper end face of the slider portion 65a, and is tapered away from the slider portion 65a. The upper edge of the support portion 65b serves as a knife edge 65c extending in the longitudinal direction of the grinding tape 10, that is, in a direction perpendicular to the sheet of FIG. 5. The knife edge 65c is received in a groove 52b of a triangular cross-section formed in the lower surface of the support rod 52 and extending in a direction perpendicular to the sheet of FIG. 5. With this arrangement, the chucking jig 51 is supported on the jig support member 65 in such a manner that the chucking jig 51 is angularly movable about the knife edge 65c serving as a fulcrum. Due to an angular moment caused by the weight of the chucking jig 51, the chucking jig 51 urges the needle materials 100 against the grinding tape 10 placed on the back-up plate 13. By loosening the fixing screws 54, the position of the first plate 53 relative to the support rod 52 can be adjusted. By this adjustment, the angular moment of the chucking jig 51 and hence the force of pressing of the needle materials 100 against the grinding tape 10 can be adjusted. In this embodiment, the pressing force is, for example, 6 g.

The lower end of the slider portion 65a of the jig support member 65 is connected to an eccentric shaft 75a of a motor (drive means) 75 via a link 76. When the motor 75 rotates, the jig support member 65 is moved upward and downward, so that the fulcrum of angular movement of the chucking jig 51 is moved upward and downward, thereby changing the angle of inclination of the needle materials 100 relative to the grinding tape 10 in a predetermined range.

The grinding of the needle materials 100 by the above grinding apparatus will now be described in detail. As described above, a number of needle materials 100 are chucked by each chucking jig 51 in such a manner that the needle materials 100 are juxtaposed in the longitudinal direction of the grinding tape 10. Each of the thus chucked needle materials 100 is disposed perpendicular to the grinding tape 10 and is inclined with respect to the surface of the grinding tape 10, and one side face of the cross-sectionally triangular portion of the needle material 100 is positioned on the grinding tape 10. Preferably, that portion of the needle material 100 to be chucked should be about one-third ($\frac{1}{3}$) of the overall length thereof. The needle materials 100 are pressed against the grinding tape 10 due to the weight of the chucking jig 51. At this time, the force of pressing of the needle materials 100 is received by the back-up plate 13, and therefore the grinding tape 10 is not flexed downwardly.

In this condition, the motor 38 of the reciprocal movement mechanism 30 is driven, so that the grinding tape 10 is reciprocally moved on the back-up plate 13 in the right and left directions (FIG. 1), thereby grinding the needle materials 100. During this reciprocal movement of the grinding tape 10, the motors 21a and 22a are stopped against rotation by their respective brakes. For example, this reciprocal movement is effected several hundreds to several thousands times at a speed of 40 m/min. over a distance of 10 mm.

When the needle materials 100 are to be thus ground by reciprocally moving the grinding tape 10 over the distance of 10 mm, it is preferred that the needle materials 100 supported by the chucking jig 51 should be spaced a distance of at least 10 mm from one another. By doing so, those regions of the grinding tape 10 for grinding the needle materials 100, respectively, do not overlap one another. However, this is not imperative, and such grinding regions may overlap one another.

After the above grinding operation is finished, the motors 21a and 22a are rotated at the same speed, so that the unused grinding tape 10 is supplied from the roll 10a, and also the used grinding tape 10 is wound on the roll 10b, thereby providing an unused portion of the grinding tape 10 onto the support surface 13a of the back-up plate 13. The speed of transfer of the grinding tape 10 is, for example, 5 mm/min. Before or after the transfer of the grinding tape 10, the lever 59 of the chucking jig 51 is angularly moved upward to weaken the force of clamping of the needle materials 100 applied by the first and second plates 53 and 57, and then the pair of set screws 62 are adjusted to move the second plate 57 relative to the first plate 53 in a direction perp endicular to the sheet of FIG. 5, thereby rolling the needle materials 100 through 120°. Thereafter, the lever 59 is laid down to again clamp the needle materials 100.

Figure 7:
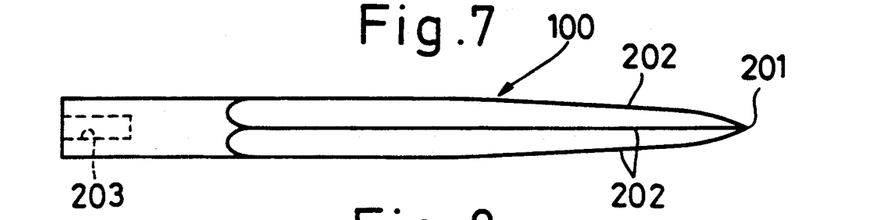
FIG. 7 is a side-elevational view of the ground needle material with its diameter shown as exaggerated.

By repeating the above procedure, the three side faces of the distal end portion of each needle material 100 are ground to form the three cutting edges 20j2. As described above, the needle materials 100 are kept inclined relative to the grinding tape 10, and in this condition are ground by the grinding tape 10. Therefore, the distal end of each needle material 100 which is not chucked by the chucking jig 51 is pointed as at 201 in FIG. 7.

During the above grinding operation, the motor 75 of the pressing mechanism 50 is rotated to reciprocally move the knife edge 65 c upward and downward once or a plurality of times, so that the angle of the needle materials 100 relative to the grinding tape 10 is changed in the predetermiend range. As a result, the angle of the cutting edge 202 relative to the axis of the needle material 100 increases progressively toward the pointed end 201.

Since the needle materials 100 are ground by the grinding tape 10 reciprocally moved several hundreds to several thousands times, the grinding tape 10 can be used without any waste. And besides, after this grinding operation, the next unused portion of the grinding tape 10 is supplied to the back-plate 13, and therefore the grinding can always be effected under the same condition. The grinding condition does not vary from one side face of the needle material 100 to another, and hence the grinding condition does not vary from one needle material 100 to another. Therefore, a required grinding condition can be obtained stably.

The tape body 10a of the grinding tape 10 is made of a synthetic resin or metal, and has the smooth surface, and the abrasive grains 10b are very fine. Therefore, even when the grinding tape 10 is reciprocally moved in the direction perpendicular to the axes of the needle materials 100, a stable grinding can be carried out. If an abrasive sheet having a substrate made of cloth or paper, part of the fibers of the substrate ar.e projected from the surface of the abrasive sheet, and such projected fibers would tend to interfere with the needle material 100 during the reciprocal movement of the abrasive sheet, so that a large bending moment would be applied to the needle material 100. In this embodiment, however, such disadvantage is not encountered.

As shown in FIG. 5, since the distal end of the chucking jig 51 can be located close to the lateral edges of the back-up plate 13 and the grinding tape 10, the needle materials 100 can be ground even if the needle materials 100 are short. Therefore, as described above, the needle material 100 can be generally equal in length to the suture needle (final product) 200. Therefore, the needle material 100 does not need to be cut after the grinding operation, and damage to the cutting edges caused by the contact between the cutting edges of the needle materials 100 during such cutting operation can be prevented. Moreover, the formation of the mounting hole 203 can be made before the grinding operation, which also can reduce the possibility of damage to the cutting edges.

In this embodiment, the six chucking jigs 51 are arranged on the lateral sides of the grinding tape 10, and each of these chucking jigs 51 supports a number of needle materials 100. Therefore, the grinding operation can be carried out efficiently.

Next, the most important advantages provided by reciprocally moving the grinding tape 10 in the direction perpendicular to the needle materials 100 will now be described. Each time each side face of the needle material 100 is ground, one ground surface is obtained. Two cutting edges 202 are formed respectively on both side edges of the ground surface. When the grinding tape 10 is moved in one direction, one of these two cutting edges 202 is disposed at a downstream side of this grinding direction, so that burrs are liable to be formed on the one cutting edge 202; however, subsequently, when the grinding tape 10 is moved in the opposite direction, the one cutting edge is disposed at an upstream side of the grinding direction so that part of the burrs can be removed. Therefore, the burrs formed on each cutting edge 202 can be reduced in size, and such burrs can be easily removed when carrying out the chemical polishing or the electropolishing after the grinding operation. Moreover, the two cutting edges 202, formed respectively on both side edges of the ground surface, have respective burrs of generally the same size, and therefore there is not encountered a disadvantage that one of the two cutting edges 202 would be excessively rounded when removing the burrs on the two cutting edges 202 by the chemical polishing or the electropolishing. As a result, the cutting edges 202 can be sharpened to generally the same level. If the cutting edges 202 are rounded when the burrs are removed by the electropolishing or the chemical polishing, such roundness is allowable if it is in an allowable range. Also, if the burrs still remain after the electropolishing and the chemical polishing, such burrs are allowable if it is in an allowable range. In this case, the burrs formed on the two cutting edges formed respectively on the opposite side edges of the ground surface are of generally the same size.

Further, since the grinding tape 10 is reciprocally moved in the direction perpendicular to the needle materials 100, the heat produced by the grinding is prevented from concentrating on the pointed end 201 of each needle material 100, thus preventing the softening of the pointed end 201.

The suture needles (hereinafter referred to as "suture needles of the invention") produced according to the above grinding method of the invention were compared with suture needles (hereinafter referred to as "conventional suture needles") produced according to the conventional grinding method shown in FIG. 14, in order to determine their piercing properties. Results obtained are as follows. When the compared suture needles had a thickness of 0.14 mm and a length of 5.5 mm, the conventional suture needle required a piercing force of 10 to 12 g whereas the suture needle of the invention only required a piercing force of 6 g. When the compared suture needles had a thickness of 0.2 mm and a length of 6.5 mm, the conventional suture needle required a piercing force of 10 to 15 g whereas the suture needle of the invention only required a piercing force of 8 g.

The present invention is not to be restricted to the above embodiment, and various modifications can be made. For example, the motors 21a and 22a may be driven to transfer the grinding tape 10 in one direction at a low speed as described above, while the grinding tape 10 is being reciprocally moved at a high speed by the motor 38.

For grinding one side face of each needle material 100, the reciprocal movement of the grinding tape 10 and the transfer of the grinding tape 10 in one direction may be alternately repeated several times.

The back-up plate 13 may be so modified that its support surface 13a has a concavely-curved shape as viewed from the end of the back-up plate 13, in which case the back-up plate 13 has a uniform cross-section throughout the entire length thereof. In this case, the needle material 100 can have the curved cutting edges corresponding in shape to the curved support surface 13a of the back-up plate 13 without the need for reciprocally moving vertically the fulcrum of angular movement of the chucking jig 51. Where the support surface 13a of the back-up plate 13 is flat, the cutting edges of the needle material 100 are straight if the fulcrum of angular movement of the chucking jig 51 is not moved.

A plurality of the back-up plates may be provided depending on the number of the pressing mechanisms.

In this case, a mechanism for adjusting the orientation of each back-up plate may be provided.

The step of forming the mounting hole in each needle material may be carried out after the grinding operation.

Figure 11:
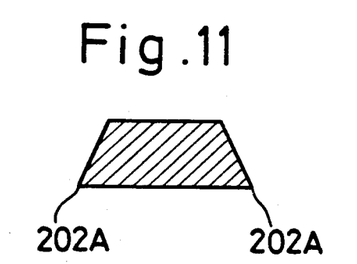
FIGS. 11 to 13 are cross-sectional views of modified suture needles, respectively.
Figure 12:
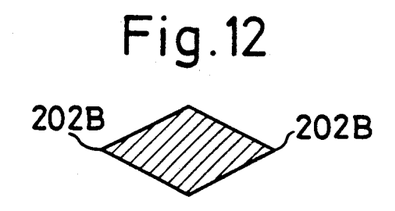
Figure 13:
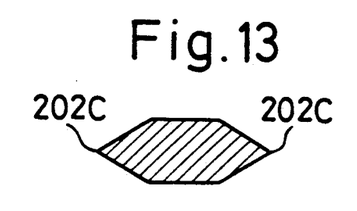

The present invention is not limited to the case of producing the suture needles of a triangular cross-section, but can be applied to the case of producing similar suture needles having any other suitable cross-section. For example, the suture needle may have the intermediate portion of a trapezoidal cross-section (FIG. 11), and the distal end portion of a triangular cross-section. In this case, the intermediate portion has two cutting edges 202A and 202A which are continuous respectively with two of the three cutting edges formed on the distal end portion. Also, the the suture needle may have a rhombic cross-section (FIG. 12) in which case two acute edges serve as cutting edges 202B and 202B, respectively. Further, the suture needle may a flatten hexagonal cross-section (FIG. 13) in which case two acute edges serve as cutting edges 202C and 202C, respectively.

What is claimed is:

1. A method of grinding an elongated material for a suture needle, comprising the step of reciprocally moving an elongated grinding tape in opposite directions along a longitudinal direction of said grinding tape, and simultaneously pressing the material against one face of said grinding tape in such a manner that the material is disposed substantially perpendicular to the longitudinal direction of said grinding tape and is inclined relative to said one face of said grinding tape, thereby grinding the material to form a cutting edge on at least one side edge of a grounded surface of the material.

2. A method according to claim 1, further comprising the step of moving said grinding tape in a predetermined one of the opposite directions along the longitudinal direction of said grinding tape after the grinding of the material by the reciprocal movement of said grinding tape is finished.

3. A method according to claim 1, further comprising the step of moving said grinding tape in a predetermined one of the opposite directions along the longitudinal direction of said grinding tape during the grinding of the material by the reciprocal movement of said grinding tape, the speed of movement of said grinding tape in said one predetermined direction being lower than the speed of reciprocal movement of said grinding tape.

4. A method according to claim 1, further comprising the step of varying the angle of inclination of said material relative to said one face of said grinding tape in a predetermined range during the grinding of the material by the reciprocal movement of said grinding tape.

* * * * *